(12) United States Patent
Van den Burg et al.

(10) Patent No.: US 6,518,054 B1
(45) Date of Patent: Feb. 11, 2003

(54) METALLO-ENDOPEPTIDASES

(75) Inventors: Lambertus Van den Burg, Epe; Oene Robert Veltman, Groningen; Gerard Venema, Haren, all of (NL)

(73) Assignee: Rijksunivserstteit Te Groningen (NL)

(*) Notice: Subject to any disclaimer, the term of this patent is extended or adjusted under 35 U.S.C. 154(b) by 0 days.

(21) Appl. No.: 09/381,982

(22) PCT Filed: Mar. 23, 1998

(86) PCT No.: PCT/NL98/00164
§ 371 (c)(1),
(2), (4) Date: Dec. 7, 1999

(87) PCT Pub. No.: WO98/44127
PCT Pub. Date: Oct. 8, 1998

(30) Foreign Application Priority Data

Mar. 27, 1997 (EP) .............................. 97200931

(51) Int. Cl.⁷ ........................... C12N 9/00; C12N 9/48; C12N 9/50; C12N 1/20; C12N 15/00
(52) U.S. Cl. .................... 435/219; 435/69.1; 435/183; 435/212; 435/252.3; 435/320.1; 435/221; 536/23.2
(58) Field of Search ................ 435/69.1, 183, 435/212, 219, 252.3, 320.1, 221; 536/23.2

(56) References Cited

PUBLICATIONS

Veltman et al. FEBS Lett., Mar. 24, 1997, vol. 405:241–244.*

* cited by examiner

Primary Examiner—Rebecca E. Prouty
Assistant Examiner—Manjunath N. Rao
(74) Attorney, Agent, or Firm—Michaelson & Wallace; Peter L. Michaelson; Arthur L. Liberman

(57) ABSTRACT

The present invention provides genes encoding variants of metallo-endopeptidases that have been engineered to be resistant to prolonged boiling while having maintained their enzymatic performance at much lower temperatures. In addition, thermal stability of the metallo-endopeptidases is highly dependent on calcium at concentrations in the mM range. The invention further provides active metallo-endopeptidases variants whose stability depending on calcium concentration can be changed so as to provide metallo-endopeptidases that are calcium dependent or independent. The invention also provides genes that encode boiling-resistant metallo-endopetidases whose stability depending on calcium concentration can be changed. The invention also provides vectors and cells comprising these genes and proteases produced through these genes, vectors and/or cells. In particular variants with the above described properties are provided of thermolysin-like proteases such as produced by *Bacillus stearothermophilus* (TLP-ste) and *Bacillus thermoproteolyticus* (thermolysine). Boiling-resistant and calcium independent or dependent metallo-endopeptidases can be applied in several industrial processes, for instance in the preparation of the artificial sweetener aspartame, but also in the leather industry, in breweries and in the production of protein hydrolysates.

13 Claims, 11 Drawing Sheets

1   Val Ala Gly Ala Ser Thr Val Gly Val Gly Arg Gly Val Leu Gly
16  Asp Gln Lys Tyr Ile Asn Thr Thr Tyr Ser(Ser Tyr Tyr)Gly Tyr
28  Tyr Tyr Leu Gln Asp Asn Thr Arg Gly Ser Gly Ile Phe Thr Tyr
43  Asp Gly Arg Asn Arg Thr Val Leu Pro Gly Ser Leu Trp Thr Asp
58  Gly Asp Asn Gln Phe Thr Ala Ser Tyr Asp Ala Ala Ala Val Asp
73  Ala His Tyr Tyr Ala Gly Val Val Tyr Asp Tyr Tyr Lys Asn Val
88  His Gly Arg Leu Ser Tyr Asp Gly Ser Asn Ala Ala Ile Arg Ser
103 Thr Val His Tyr Gly Arg Gly Tyr Asn Asn Ala Phe Trp Asn Gly
118 Ser Gln Met Val Tyr Gly Asp Gly Asp Gly Gln Thr Phe Leu Pro
133 Phe Ser Gly Gly Ile Asp Val Val Gly His Glu Leu Thr His Ala
148 Val Thr Asp Tyr Thr Ala Gly Leu Val Tyr Gln Asn Glu Ser Gly
163 Ala Ile Asn Glu Ala Met Ser Asp Ile Phe Gly Thr Leu Val Glu
178 Phe Tyr Ala Asn Arg Asn Pro Asp Trp Glu Ile Gly Glu Asp Ile
193 Tyr Thr Pro Gly Val Ala Gly Asp Ala Leu Arg Ser Met Ser Asp
208 Pro Ala Lys Tyr Gly Asp Pro Asp His Tyr Ser Lys Arg Tyr Thr
223 Gly Thr Gln Asp Asn Gly Gly Val His Thr Asn Ser Gly Ile Ile
238 Asn Lys Ala Ala Tyr Leu Leu Ser Gln Gly Gly Val His Tyr Gly
253 Val Ser Val Asn Gly Ile Gly Arg Asp Lys Met Gly Lys Ile Phe
268 Tyr Arg Ala Leu Val Tyr Tyr Leu Thr Pro Thr Ser Asn Phe Ser
283 Gln Leu Arg Ala Ala Cys Val Gln Ala Ala Ala Asp Leu Tyr Gly
298 Ser Thr Ser Gln Glu Val Asn Ser Val Lys Gln Ala Phe Asn Ala
313 Val Gly Val Tyr

| | | | | | | | | | | | | | | | |
|---|---|---|---|---|---|---|---|---|---|---|---|---|---|---|---|
| 1 | Val | Ala | Gly | Ala | Ser | Thr | Val | Gly | Val | Gly | Arg | Gly | Val | Leu | Gly |
| 16 | Asp | Gln | Lys | Tyr | Ile | Asn | Thr | Thr | Tyr | Ser | Ser | Tyr | Tyr | Gly | Tyr |
| 31 | Tyr | Tyr | Leu | Gln | Asp | Asn | Thr | Arg | Gly | Ser | Gly | Ile | Phe | Thr | Tyr |
| 46 | Asp | Gly | Arg | Asn | Arg | Thr | Val | Leu | Pro | Gly | Ser | Leu | Trp | Thr | Asp |
| 61 | Gly | Asp | Asn | Gln | Phe | Thr | Ala | Ser | Tyr | Asp | Ala | Ala | Ala | Val | Asp |
| 76 | Ala | His | Tyr | Tyr | Ala | Gly | Val | Val | Tyr | Asp | Tyr | Tyr | Lys | Asn | Val |
| 91 | His | Gly | Arg | Leu | Ser | Tyr | Asp | Gly | Ser | Asn | Ala | Ala | Ile | Arg | Ser |
| 106 | Thr | Val | His | Tyr | Gly | Arg | Gly | Tyr | Asn | Asn | Ala | Phe | Trp | Asn | Gly |
| 121 | Ser | Gln | Met | Val | Tyr | Gly | Asp | Gly | Asp | Gly | Gln | Thr | Phe | Leu | Pro |
| 136 | Phe | Ser | Gly | Gly | Ile | Asp | Val | Val | Gly | His | Glu | Leu | Thr | His | Ala |
| 151 | Val | Thr | Asp | Tyr | Thr | Ala | Gly | Leu | Val | Tyr | Gln | Asn | Glu | Ser | Gly |
| 166 | Ala | Ile | Asn | Glu | Ala | Met | Ser | Asp | Ile | Phe | Gly | Thr | Leu | Val | Glu |
| 181 | Phe | Tyr | Ala | Asn | Arg | Asn | Pro | Asp | Trp | Glu | Ile | Gly | Glu | Asp | Ile |
| 196 | Tyr | Thr | Pro | Gly | Val | Ala | Gly | Asp | Ala | Leu | Arg | Ser | Met | Ser | Asp |
| 211 | Pro | Ala | Lys | Tyr | Gly | Asp | Pro | Asp | His | Tyr | Ser | Lys | Arg | Tyr | Thr |
| 226 | Gly | Thr | Gln | Asp | Asn | Gly | Gly | Val | His | Thr | Asn | Ser | Gly | Ile | Ile |
| 241 | Asn | Lys | Ala | Ala | Tyr | Leu | Leu | Ser | Gln | Gly | Gly | Val | His | Tyr | Gly |
| 256 | Val | Ser | Val | Asn | Gly | Ile | Gly | Arg | Asp | Lys | Met | Gly | Lys | Ile | Phe |
| 271 | Tyr | Arg | Ala | Leu | Val | Tyr | Tyr | Leu | Thr | Pro | Thr | Ser | Asn | Phe | Ser |
| 286 | Gln | Leu | Arg | Ala | Ala | Cys | Val | Gln | Ala | Ala | Ala | Asp | Leu | Tyr | Gly |
| 301 | Ser | Thr | Ser | Gln | Glu | Val | Asn | Ser | Val | Lys | Gln | Ala | Phe | Asn | Ala |
| 316 | Val | Gly | Val | Tyr | | | | | | | | | | | |

Figure 7B

```
1    Val Ala Gly Ala Ser Thr Val Gly Val Gly Arg Gly Val Leu Gly
16   Asp Gln Lys Tyr Ile Asn Thr Thr Tyr Ser Gly Tyr
28   Tyr Tyr Leu Gln Asp Asn Thr Arg Gly Ser Gly Ile Phe Thr Tyr
43   Asp Gly Arg Asn Arg Thr Val Leu Pro Gly Ser Leu Trp Thr Asp
58   Gly Asp Asn Gln Phe Thr Ala Ser Tyr Asp Ala Ala Ala Val Asp
73   Ala His Tyr Tyr Ala Gly Val Val Tyr Asp Tyr Tyr Lys Asn Val
88   His Gly Arg Leu Ser Tyr Asp Gly Ser Asn Ala Ala Ile Arg Ser
103  Thr Val His Tyr Gly Arg Gly Tyr Asn Asn Ala Phe Trp Asn Gly
118  Ser Gln Met Val Tyr Gly Asp Gly Asp Gly Gln Thr Phe Leu Pro
133  Phe Ser Gly Gly Ile Asp Val Val Gly His Glu Leu Thr His Ala
148  Val Thr Asp Tyr Thr Ala Gly Leu Val Tyr Gln Asn Glu Ser Gly
163  Ala Ile Asn Glu Ala Met Ser Asp Ile Phe Gly Thr Leu Val Glu
178  Phe Tyr Ala Asn Arg Asn Pro Asp Trp Glu Ile Gly Glu Asp Ile
193  Tyr Thr Pro Gly Val Ala Gly Asp Ala Leu Arg Ser Met Ser Asp
208  Pro Ala Lys Tyr Gly Asp Pro Asp His Tyr Ser Lys Arg Tyr Thr
223  Gly Thr Gln Asp Asn Gly Gly Val His Thr Asn Ser Gly Ile Ile
238  Asn Lys Ala Ala Tyr Leu Leu Ser Gln Gly Gly Val His Tyr Gly
253  Val Ser Val Asn Gly Ile Gly Arg Asp Lys Met Gly Lys Ile Phe
268  Tyr Arg Ala Leu Val Tyr Tyr Leu Thr Pro Thr Ser Asn Phe Ser
283  Gln Leu Arg Ala Ala Cys Val Gln Ala Ala Ala Asp Leu Tyr Gly
298  Ser Thr Ser Gln Glu Val Asn Ser Val Lys Gln Ala Phe Asn Ala
313  Val Gly Val Tyr
```

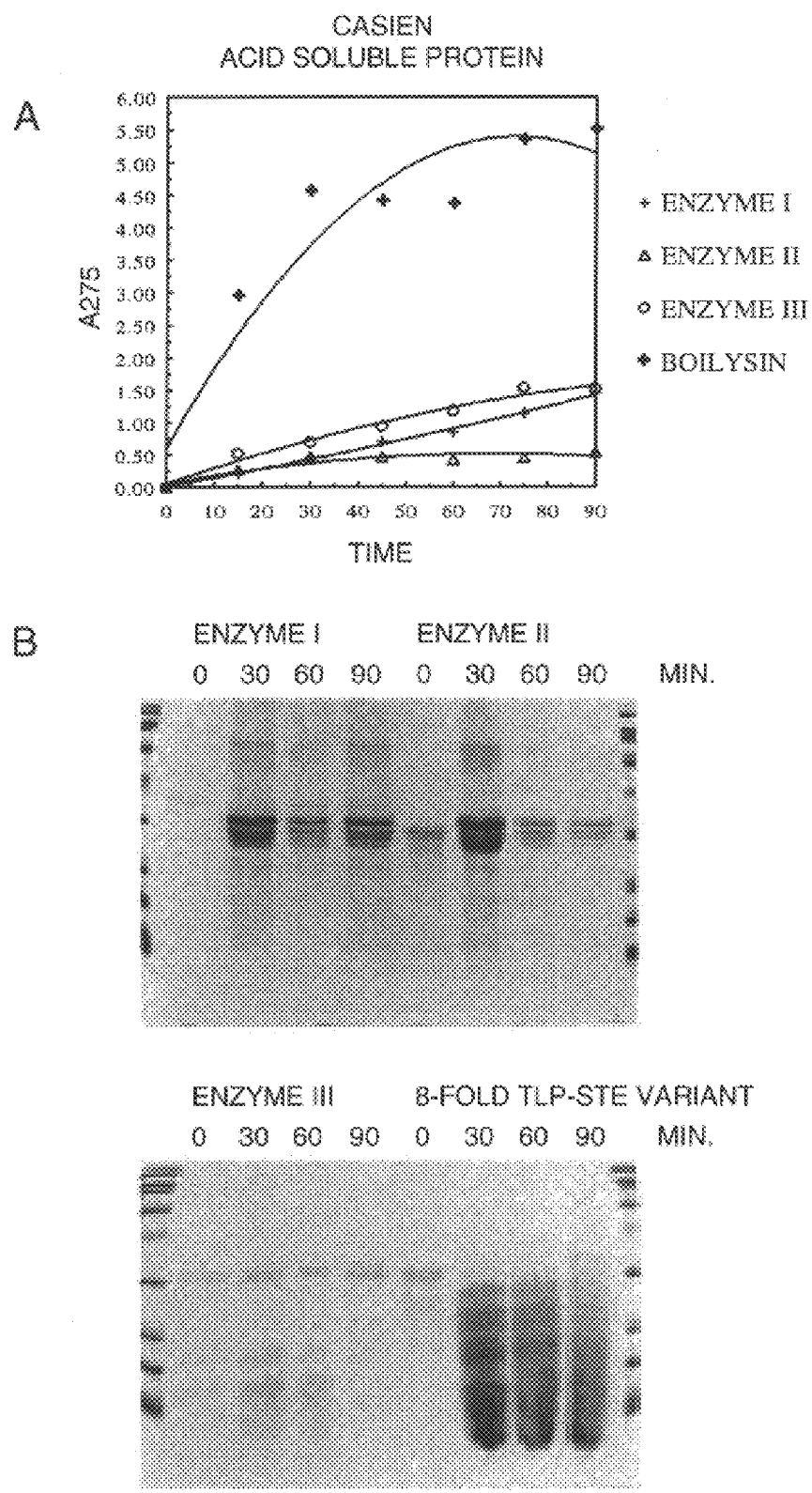
Fig. 8  Hydrolysis of 10% (w/v) casein by different enzyme preparations (0.05%, v/v).

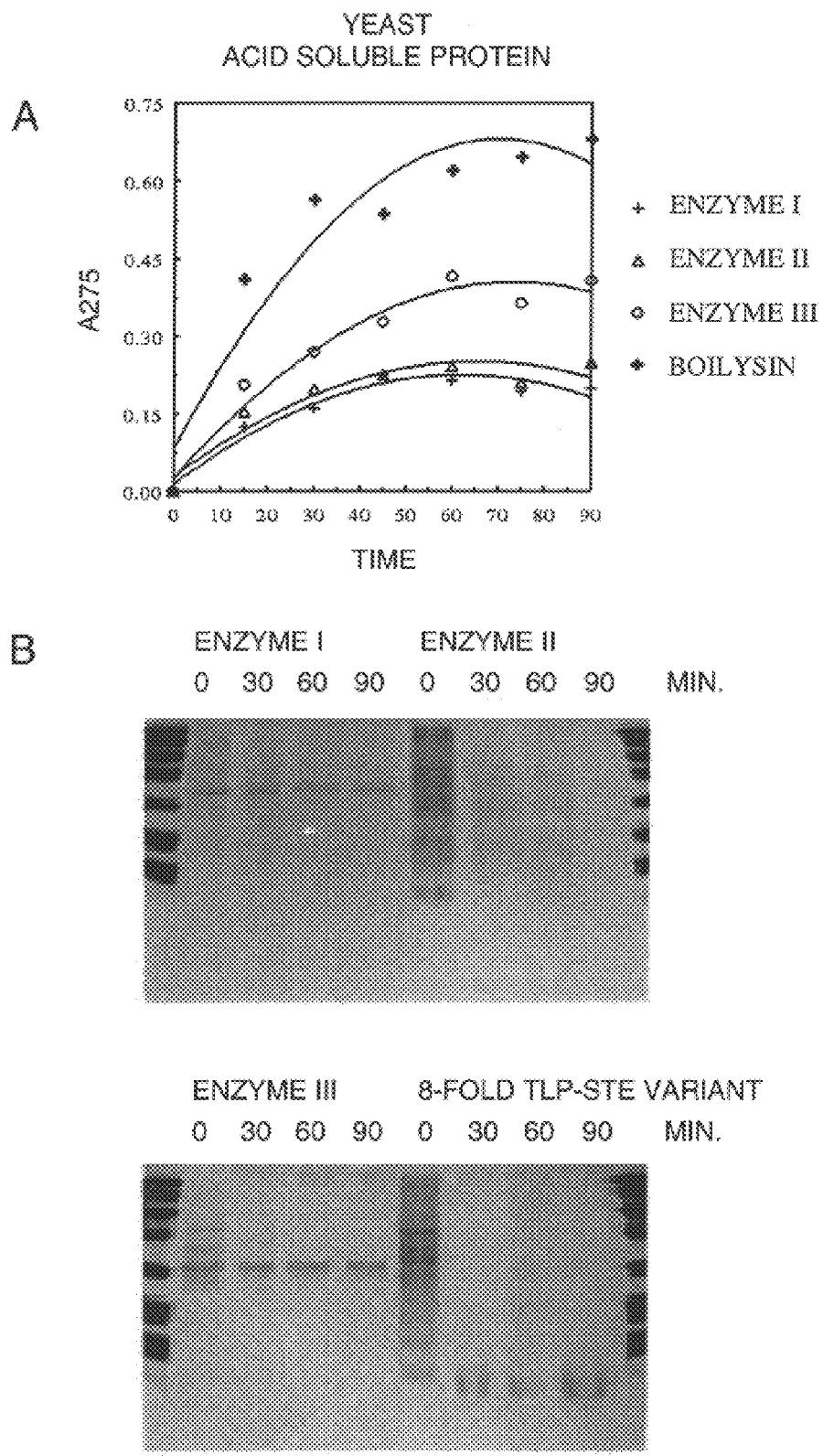
Fig. 9  Hydrolysis of 10% (w/v) yeast proteins by different enzyme preparations (0.05%, v/v).

METALLO-ENDOPEPTIDASES

The present invention relates to metallo-endopeptidases, sometimes also called neutral proteases, that are produced, processed and secreted by e.g. members of the bacterial genus Bacillus. The present invention provides genes encoding variants of metallo-enopeptidases that have been engineered to be resistant to prolonged boiling while maintaining their enzymatic performance at much lower temperatures. In addition, thermal stability of the metallo-endopeptidases is highly dependent on calcium at concentrations in the mM range. The invention thus further provides active metallo-endopeptidase variants whose stability depending on calcium concentration can be changed so as to provide metallo-endopeptidases that are calcium dependent or independent. The invention also provides genes that encode boiling-resistant metallo-endopeptidases whose stability depending on calcium concentration can be changed. The invention also provides vectors and cells comprising these genes and proteases produced through these genes, vectors and/or cells.

Denaturation of proteins at elevated temperatures is usually the result of unfolding which is followed by an irreversible process, most often aggregation. The notion that the unfolding processes involved in irreversible denaturation often have a partial (as opposed to global) character has been confirmed experimentally in several cases. We have studied the thermal stability and denaturation of a broad-specificity metalloprotease produced by *Bacillus stearothermophilus* CU21 (called TLP-ste) which shares 85% sequence identity with its more stable and better known counterpart *Bacillus thermoproteolyticus* (hereinafter also referred to as "thermolysin"). Thermolysin-like proteases (TLPs) are a family of homologous metalloproteases or neutral proteases that contain a catalytically important zinc ion in their active site. Thermal denaturation of thermolysin-like proteases (TLPs) depends on partial unfolding processes as well, which, however, are not followed by aggregation but by autolytic degradation starting at unknown sites in the partially unfolded molecule (Vriend, G. & Eijsink, V. G. H. J. *Comput.-Aided Mol. Des.* 7, 367–396, 1993). An extensive mutation study in which residues in TLP-ste were replaced via site-directed mutagenesis by the corresponding amino acid in thermolysin showed that only a few of the 43 substitutions between the two enzymes are important for stability (Veltman, O. R., Vriend, G., Middelhoven, H., Van den Burg, B., Venema, G. & Eijsink, V. G. H. *Protein Engn.* 9, 1181–1189, 1996). All important substitutions are clustered in the N-terminal domain of the protein, in particular in a weak region comprising the 55–69 surface loop (European patent application 94200182.7). Remarkably, stabilizing substitutions or combinations of several substitutions either (i) at the positions of SEQUENCE ID No. 2: 4, 56, 58, 63, 65 or 69 (for example A4T, T56A, G58A, T63F, S65P, A69P) or (ii) the positions of SEQUENCE ID No. 1: 4, 59, 61, 66, 68 or 72 (for example A4T, T59A, G61A, T66F, S68P, A72P) result in enzyme variants that are more stable than thermolysin. The three-dimensional structure of thermolysin is known (Holmes, M. A. and Matthews, B. W. (1982) J. Mol. Biol, 160, 623–639) and this enzyme was shown to bind four calcium atoms which contribute to thermal stability. Two calcium ions are bound in the so-called double-calcium binding site ($Ca_{1,2}$), that is composed of ligands that are conserved in all TLPs. The other, single binding sites ($Ca_3$ and $Ca_4$) are composed of ligands that are conserved only in the more stable TLPs such as thermolysin and the TLP produced by *B. stearothermophilus* (TLP-ste). At elevated temperatures, TLPs are irreversibly inactivated as a consequence of autolysis. Autolysis follows first-order kinetics because its rate is determined by local unfolding processes that render the protease susceptible to autoproteolytic cleavage (Eijsink, V. G. H., Van den Burg. B., Vriend, G., Berendsen, H. J. C. and Venema, G. (1991) Biochem. Internatl. 24, 517–525). In their studies on the contribution of calcium ions to thermolysin stability, Dahlquist et al. (Dahlquist, F. W., Long, J. W, and Bigbee, W. L. (1976) Biochemistry 15, 1103–1111. ) and Roche and Voordouw (Roche, R. S. and Voordouw, G. (1978) CRC Crit. Rev. Biochem. 5, 1–23) concluded that the initial steps in thermal inactivation are accompanied by the release of one calcium ion ($Ca_3$ or $Ca_4$). Extensive mutagenesis studies of the TLP-ste have shown that a region near the $Ca_3$ site is crucial for thermal stability (Veltman, O. R., Vriend, G., Middelhoven, P. J., Van den Burg, B., Venema, G. and Eijsink, V. G. H. (1996) Protein Engng. 9, 1181–1189. ). Thus, thermal inactivation seems to be dominated by one single 'weak' region, near $Ca_3$. Considering the expected high structural similarity between thermolysin and TLP-ste (85 percent sequence identity) the studies on TLP-ste suggest that the critical calcium ion is $Ca_3$ rather than $Ca_4$.

Metallo endopeptidases can be applied in several industrial processes, for instance in the preparation of the artificial sweetener aspartame, but also in the leather industry, for dehairing or dewooling, in breweries and in the production of (poly)peptide or protein hydrolysates. These processes may need to be performed at high temperatures to accelarate the processes. However, the enzymes used normally are not resistant to elevated temperatures. Proteases that are more stable at higher temperatures can for example be obtained via mutations in the 55–69 area, however, they still do not withstand boiling for periods lasting longer than several minutes. On the other hand, boiling is a simple method to denature the enzyme and thus a method to stop the enzymatic process. Thus, there is a need to develop enzymes that are more resistant to the temperatures found at boiling for prolonged periods in a watery environment, with an half-life >0.5 hour at 100° C. but that on the other hand, if needed, may be controlled by other methods to stop the enzymatic processes.

The invention provides strategies to design and construct genetically engineered thermolysine-like proteases that are far more resistant to boiling than those known before. The invention also provides the proteases resulting from such strategies as well as the use of said products in industrial processes and intermediates in making the products. The invention provides mutations leading to the introduction of disulfide bridges stabilizing the area in metallo-endopeptidases that is most susceptible to unfolding after heating which area is hereinafter referred to as the "functional part of the sequence". In a first embodiment, the invention provides a recombinant DNA molecule comprising a least a functional part of the sequence of FIG. 7 and coding functional part of the sequence of FIG. 7A [SEQUENCE ID No. 1] or FIG. 7B [SEQUENCE ID No. 2] or FIG. 7 (which combines the SEQUENCE ID No. 1 and the SEQUENCE ID No. 2 as more fully explained, infra) coding wherein at least one codon is mutated to code for cysteine to generate a stabilizing disulfide bridge, and a polypeptide derived of said DNA molecule. For example, an important mutation concerns the introduction of a disulfide bridge cross-linking residue 60 [in SEQUENCE ID No. 2] or residue 63 [in SEQUENCE ID No. 1] in the critical region with residue 8 (common to each of SEQUENCE ID No. 1 and SEQUENCE ID No. 2) in the underlying β-hairpin. For example, the invention provides a mutated TLP-ste variant with a half life at 100° C. of almost 3 hours which is more than 1000 times that of the wild-type while it maintained its specific activity at 37° C. Furthermore, the invention provides mutants that are active and stable in the presence of high concentrations of denaturing agents and which cleavage specificity at both moderate and high temperatures is largely unaffected by the stabilizing mutations.

The invention also provides calcium-dependent and—independent variants of thermolysine-like proteases. Another embodiment of the invention is a recombinant DNA molecule comprising a least a functional part of the sequence of FIG. 7B (SEQUENCE ID No. 2) or FIG. 7A (SEQUENCE ID No. 1) coding for a polypeptide having metallo-endopeptidase activity wherein at least one codon is mutated to code for an amino-acid providing the resulting gene product (polypeptide) with a reduced capacity to bind with calcium.

For example, (i) referring to FIG. 7B (SEQUENCE ID No. 2), the $Ca_3$ binding site of TLP-ste was deteriorated by mutating one of the main ligands (Asp57), but substitutions T63F or A69P leave the calcium-dependent stability intact, and (ii) referring to FIG. 7A (SEQUENCE ID No. 1), the $Ca_3$ binding site of TLP-ste was deteriorated by mutating one of the main ligands (Asp60) but substitutions T66F or A72P leave the calcium-dependent stability intact. Subsequently, the loss in stability is compensated for by introducing stabilising mutations in the direct environment of the $Ca_3$ site. The results confirm the importance of the $Ca_3$ site for stability and they show the feasibility of engineering various grades of calcium-dependency in otherwise stable variants.

In addition, by combining above substitutions, the invention provides variants that encode boiling-resistant metallo-endopetidases whose stability depending on calcium concentration can be changed. For example, the invention further provides a recombinant DNA molecule wherein (i) in SEQUENCE ID No. 2 at least one codon coding for A at position 4, or T at 56, or G at 58, or T at 63, or S at 65, or A at 69 is mutated; for example, wherein at least one codon encoding the amino acid at position 4 is replaced by a codon encoding T, or at position 56 by a codon encoding A, or at position 58 by a codon encoding A, or at position 63 by a codon encoding F, or at position 65 by a codon encoding P, or at position 69 by a codon encoding P, and (ii) in SEQUENCE ID No. 1 at least one codon coding for A at position 4, or T at 59, or G at 61, or T at 66, or S at 68, or A at 72 is mutated; for example, wherein at least one codon encoding the amino acid at position 4 is replaced by a codon encoding T, or at position 59 by a codon encoding A, or at position 61 by a codon encoding A, or at position 66 by a codon encoding F, or at position 68 by a codon encoding P, or at position 72 by a codon encoding P. In yet another embodiment of the invention, a recombinant DNA molecule is provided wherein, referring to each of SEQUENCE ID No. 1 and SEQUENCE ID No. 2, the codon coding for G at position 8 has been modified to code for cysteine (C) or wherein (i) referring to SEQUENCE ID No. 2 the codon coding for D at position 57 has been mutated to code for serine, or (ii) referring to SEQUENCE ID No. 1 the codon coding for D at position 60 has been mutated to code for serine. The invention also provides a vector for expression of a polypeptide having metallo-endopeptidase activity, and provides a host cell expressing said polypeptide, comprising said vector. A polypeptide expressed by such a host cell has a high metallo-endopeptidase activity, especially when compared with conventionally used enzyme preparations, as for example shown in the experimental part of this description. One polypeptide as provided by the invention has for example a metallo-endopeptidase activity having a half-life in a watery environment at 100° C. that is >0.5 hours. It goes without saying that such a high-active and stable enzyme has a wide range of uses, for example for the production of (poly)peptides or protein hydrolysates.

Industrial proteins, such as derived from soy, rice, milk, yeast, gluten, and other dietary proteins (such as animal food, fish protein) can now more easily be hydrolised or predigested, for example to increase its dietary value. Also, an hydrolysing enzyme as provided by the invention can be used to help clean (by hydrolysis) medical instruments under relatively mild conditions. Yet another use as provided by the invention is in cleaning (industrial) membranes and filters, in cleaning heat exchangers or condensers, or in any other instrument where deposits of proteins can be found that need removal. Specific hydrolysis, as provided by an enzyme provided by the invention is a new effective way of removing protein for example during waste water treatment. Small scale use is possible in cleaning contact lenses, surgical implants, and the like. In the laboratory, glassware and intruments can be cleaned more easily. Also preparation of DNA, freeing it from contamination protein in samples wherein nucleic acid is sought, is now more readily feasible. An enzyme provided by the invention can be used in pure or isolated form, or mixed with other components, such as with a detergent, or in washing powders, to provide synergistic action. Use as provided by the invention can for example be in the production of aspartame, for the production of leather, for dehairing or dewooling or in detergents or washing powders. Yet other examples are use for treatment of slaughter offal, optionally for the preparation of protein hydrolysates for commercial purposes. The invention provides use of a polypeptide as provided by the invention in hydrolysing protease resistant proteins. An example of such a use of a polypeptide provided by the invention is in hydrolysis of proteins that are more than an average protein resistant to hydrolysis. One example is hydrolysis of protease resistant α-amylase by a polypeptide as provided by the invention, another example is hydrolysis of prion protein, which is also very resistant to proteolytic cleavage. Prion protein hydrolysis for example is very beneficial in cleaning medical instruments or testing apperature, without having to resort to extreme chemical or temperature treatments. Also, pretreatment of clinical samples in which prion protein may be detected (i.e. by ELISA) can now also be done more easily, whereby varying the assay conditions allows for early digestion of contaminating proteins, leaving the prion protein relatively intact. Because of its high activity and stability at higher temperatures, such a use of a polypeptide is preferred. This allows for rapid processes or processing of a large amount per treatment. For instance during pasteurisation or sterilisation treatment of food, contaminants in food, such as micro-organisms, or the above mentioned prion protein, or other proteinaceous contaminants can be rendered uninfectious by treating said food or feed (for both human or animal consumption) (possibly containing any of above mentioned proteinaceous contaminants) with a polypeptide provided by the invention. It is even possible to shorten temperature treatment because of the high activity of said polypeptide.

EXPERIMENTAL PART

2. Materials and Methods 2.1 Production and Characterisation of Mutated Enzymes

Cloning, sequencing, sub-cloning, and expression of the TLP-ste gene (from strain *B. stearothermophilus* CU21), as well as production, purification and subsequent characterization of wild-type and mutant TLP-ste were performed as described earlier (Eijsink, V. G. H., Vriend, G., Van der Vinne, B., Hazes, B., Van den Burg, B. and Venema, G. (1992) Proteins 14, 224–236). Thermal stability was measured, using varying $CaCl_2$ concentrations in the standard assay buffer (20 mM Na acetate, pH 5.3, 0.01% Triton X-100, 0.5% isopropanol, 62.5 mM NaCl). $T_{50}$ is the temperature of incubation at which 50 percent of the initial proteolytic activity is lost during a 30 minutes incubation.

The kinetic parameter $k_{cat}/K_m$ (at 37° C.) for the substrate 3-(-2-furylacryloyl)-L-glycyl-L-leucine-amide (FaGLa, Sigma Chemical Company, St. Louis, Mich., USA) was determined according to the method of Feder et al. (Feder, J. (1969) Biochemistry 6, 2088–2093), in a buffer containing 50 mM Tris-HCl, pH 7.5, 5 mM $CaCl_2$, 5% or 1% DMSO, 1% isopropanol and 125 mM NaCl, using an 100 mM substrate concentration. Activities were derived from the decrease in absorption at 345 nm, using a Deof $-317$ $M^{-1}$ $cm^{-3}$.

Specific activities for TLP-ste and the 8-fold mutant were determined using casein (0.8%) as a substrate in 50 mM Tris-HCl (pH 7.5), 5 mM $CaCl_2$ at 37° C. The $k_{cat}/K_m$ values for the enzymes were determined for two different furylacryloylated dipeptides as substrates, at 37° C. in a thermostatted Perkin Elmer Lambda 11 spectrophotometer, in a total volume of 1 ml of 50 mM MOPS [4-morpholineethanesulfonic acid] (pH 7.0), 5 mM $CaCl_2$, 5% or 1% DMSO, 0.5% isopropanol, 0.01% Triton X-100, 50 mM NaCl, with 100 mM of substrate, by measuring the decrease in absorption at 345 nm ($Î_{345}=-317$ $M^{-1} \cdot cm^{-1}$). Stock solutions of the furylacryloylated dipeptides, (Sigma, St. Louis, Mich.) were prepared by dissolving 3-(-2-furylacryloyl)-L-glycyl-L-leucine amide (FaGLa) and 3-(-2-furylacryloyl)-L-alanyl-L-phenylalanine amide (FaAFa) in DMSO. The $k_{cat}/K_m$ ratios of the enzymes were determined by varying the enzyme concentrations (over a 50 fold range) under pseudo-first order conditions by measuring the initial activity, essentially according to the method described by Feder[30]. The $K_i$ for phosphoramidon (N-[a-L-rhamnopyrano-syl-oxyhydroxyphophinyl]-L-leucyl-L-tryptophan) was determined by a 30 minute preincubation of a 100 pM protease solution with varying concentrations of the inhibitor ($10^{-8}$ to $10^{-3}$ M), in 50 mM MOPS (pH 7.0), 5 mM $CaCl_2$, 50 mM NaCl, prior to the addition of the furylacryloated substrate. For determination of the $K_i$ FaAFa was used as the substrate. Since the $K_m$ of the substrate for the enzyme is higher than the concentration used, $IC_{50}$ values were taken to be equal to $K_i$ values. The optimum temperature for activity was determined by incubating proteases with casein (0.8%) in 50 mM Tris-HCl (pH 7.5), 5 mM $CaCl_2$, at different temperatures for 30 minutes, after which the amount of released peptides, indicative for activity, was measured[11].

Protease activities were determined in 50 mM MOPS (pH 7.0), 5 mM $CaCl_2$, 50 mM NaCl, 0.01% Triton X-100, 0.5% isopropanol, using 100 μM FaGLa (3-(-2-furylacryloyl)-L-glycyl-L-leucine amide) as a substrate at 50° C. Enzymes and denaturing agents were preincubated in the reaction mixture at 50° C. for 15 minutes prior to the addition of the substrate. The reaction was followed by measuring the change in absorbance at 345 nm. The change in absorbance was linear during the time of measurement (30–60 minutes), indicating that the proteases were stable in this time interval and that substrate depletion was negligible. Activities are expressed as percentage of the activity in the absence of denaturant.

2.2 Structure Analysis

TLP-ste and thermolysin have 85% sequence identity which allowed the construction of a three dimensional model of TLP-ste that is sufficiently reliable to predict the effects of site directed mutations (Vriend, G. and Eijsink, V. G. H. (1993) J. Comput. Aided. Mol. Des. 7, 367–396.). The 55–69 (referring to FIG. 7, FIG. 7B and SEQUENCE ID No. 2) region was expected to be highly similar in TLP-ste and thermolysin. Comparison of the two known TLP structures, thermolysin and the TLP from B. cereus (Stark, W., Pauptit, R. A., Wilson, K. S. and Jansonius, J. N. (1992) Eur. J. Biochem., 207, 781–791) supported this: TLP-cer has lower homology to thermolysin (73% sequence identity) but, nevertheless has a strikingly similar fold in the 55–69 (referring to FIG. 7, FIG. 7B and SEQUENCE ID No. 2) region (the RMS positional difference is in the order of a few tenths of an Angstrom, that is, in the order of the crystallographic error). Indeed, the TLP-ste model has been used successfully for the rational design of stabilising mutations (Mansfeld, J., Vriend, G., Dijkstra, B. W., Venema, G., Ulbrich-Hofmann, R. and Eijsink, V. G. H. (1995) in: Perspectives on Protein Engineering. (Geisow, M. J. and Epton, R. eds), pp. 205–206, Mayflower, Worldwide Ltd, Birmingham, UK). Structure analyses, three dimensional modelling, prediction of the effects of point mutants, and data base searches were performed with the WHAT IF program (Vriend, G. (1990) J.Mol.Graphics, 8, 52–56). Referring to FIG. 7, described in detail, infra, the only insertion/deletion in the alignment of thermolysin (316 residues) and TLP-ste (319 residues) is a three residue insertion between residues 25 and 30 in TLP-ste. In FIG. 7, this insertion was omitted in the numbering of TLP-ste sequence, meaning that TLP-ste residues are numbered according to the corresponding residues in thermolysin. In the instant application, however, two separate sequences (each with conventional sequence numbering)are shown: (i) FIG. 7A (SEQUENCE ID No. 1) for the TLP-ste (319 residues) and (ii) FIG. 7B (SEQUENCE ID No. 2) for the thermolysin (316 residues).

3. Results and Discussion

We set out to search for several additional stabilizing mutations in the 55–69 area (with reference to FIGS. 7 and 7B and SEQUENCE ID No. 2). One mutation, a Ser® Pro mutation at position 65 in SEQUENCE ID No. 2 (corresponding to position 68 in SEQUENCE ID No. 1), has been described previously, and did not add anything new to previous strategies. The second and most important mutation concerns a very different strategy, away from modifying the weak region. It concerns the introduction of a disulfide bridge cross-linking residue 60 (in SEQUENCE ID No. 2) and residue 63 (in SEQUENCE ID No. 1) in the critical region with residue 8 in the underlying β-hairpin (FIG. 1). The resulting 8-fold mutated TLP-ste variant is the most stable enzyme ever obtained by protein engineering, with a half life at 100° C. of almost 3 hours (Table 1 and FIG. 2).

The half-life of the 8-fold mutant at 100° C. was more than 1000 times that of the wild-type and the temperature for optimum activity was raised by 21° C. The specific activities at 37° C. were identical for the wild-type TLP-ste and the 8-fold mutant (Table 1). In contrast to the wild-type, the 8-fold mutant was active and stable in the presence of high concentrations of denaturing agents (Table 2). The cleavage specificity at both moderate and high temperatures was largely unaffected by the stabilizing mutations (Table 1 and FIG. 3). In summary, the enzymatic properties of the constructed variant resemble those of the wild-type, but its stability resembles that of extremozymes or thermozymes produced by organisms that are capable of surviving in extreme environments such as Archaea and Eubacterial extremophiles.

As an example of the enzymatic activity of the 8-fold mutant we tested the hydrolysis of protease resistant α-amylase from Bacillus licheniformis by the 8-fold mutant. B. licheniformis α-amylase (1 mg/ml) in 50 mM MOPS, pH 7.0, 5 mM $CaCl_2$, 0.01% Triton X-100 was incubated with purified TLP-ste (1 μg/ml), the 8-fold mutant or without protease for 60 minutes at the temperature indicated. The reaction volume was 500 μL. After incubation the samples were cooled on ice, which resulted in aggregation of the substrate in the samples that had been incubated at 100° C. Precipitates (only observed in the 100° C. samples) were collected by centrifugation and redissolved in 500 μL 6 M Urea. Both supernatants and redissolved precipitates were subjected to standard SDS-PAGE, including pre-treatment with sample loading buffer (5 minutes at 100° C.). The samples were identical in size (20 μL supernatant and 20 μL dissolved precipitate). Gels were stained with Coomassie-brilliant blue. No significant degradation of α-amylase occurred at temperatures of 80° C. and lower, irrespective of the enzyme used. In case the samples were incubated at 100° C. without added protease or with TLP-ste the aggregate formed after cooling contained mature α-amylase, indicating that no hydrolysis had occurred. The B. licheniformis α-amylase that was incubated with the 8-fold mutant at 100° C. was completely hydrolysed and no aggregate was formed.

Studies on proteins from extremophiles have revealed that adaptation to extreme environments can normally be attributed to intrinsic properties of these proteins, although in some cases contributions of particular intracellular components, e.g. heat shock proteins and so-called "thermoprotectants", have been demonstrated. The number of extremozymes for which the structure and sequence could be compared with mesophilic counterparts is limited. On the basis of comparative studies of the primary structures of proteins from mesophilic and thermophilic organisms general rules for stability have been proposed. It has been observed that extremozymes are often less active at lower temperatures than their mesophilic counterparts. The present results, however, lead to the unexpected but important conclusion that it is possible to engineer extremozymes that retain their full activity at lower temperatures.

The present study shows that boiling-resistant proteins can be obtained by rational design. The key to success is insight in the often local and unpredictable unfolding processes that determine the rate of irreversible thermal inactivation. Rationally designed extremozymes can be valuable biocatalysts, as exemplified by the ability of the 8-fold TLP-ste mutant to hydrolyse stable, protease-resistant substrates. With respect to applications, it is most important to note that the 8-fold mutant displays adaptation to extreme conditions without forfeiture of enzymatic performance.

With regard to calcium binding (referring to FIGS. 7A and 7B and SEQUENCE ID No. 2), it was found that from a structural point of view Asp57 seemed more important for calcium binding than Asp59 because both Ods of Asp57 interact with the calcium versus only one Od of Asp59 (FIG. 4). Asp57 was replaced by Ser because in the less thermostable TLPs residue 57 is a serine. From a visual inspection of the three dimensional environment of residue 57 it was concluded that the D57S mutation would not have additional negative effects such as disturbance of the local hydrogen bonding network or the introduction of clashes. To compensate the expected destabilising effect of this mutation, the combined T63F-A69P mutation was chosen. The stabilising mutations had been identified in previous site-directed mutagenesis studies of differences between naturally occurring TLPs (Van den Burg, B., Enequist, H. G., Van der Haar, M. E., Eijsink, V. G. H., Stulp, B. K. and Venema, G. (1991) J. Bacteriol. 173, 4107–4115) and in studies concerning the design of stabilising Xxx->Pro mutations in TLP-ste (Hardy, F., Vriend, G., Veltman, O. R., van der Vinne, B., Venema, G. and Eijsink, V. G. H. (1993) FEBS Lett. 317, 89–92). The mutations are located in the direct environment of $Ca_3$ and the double mutation had previously been shown to drastically stabilise TLP-ste. Characteristics of the various mutants, including the dependence of stability on calcium concentration are presented in Tables 5 and 6 and in FIGS. 5 and 6. As shown in Table 5, the wild-type and mutant enzymes were similar with respect to their activity towards FaGLa.

Referring to FIGS. 7 and 7B and SEQUENCE ID No. 2, the D57S mutation reduced the $T_{50}$ of TLP-ste at 12.5 mM calcium from 77.9° C. to 69.4° C. (Table 4). In the stable T63F-A69P mutant the effect of the D57S mutation was even more noticeable, and reduced Tso from 90.2° C. to 77.2° C. Thus, the integrity of the $Ca_3$ site is clearly important for TLP-ste's thermal stability.

The stability of TLP-ste and the T63F-A69P mutant (referring to FIGS. 7A and 7B and SEQUENCE ID No. 2) (which both have the $Ca_3$ site intact) depended strongly on the calcium concentration (FIG. 5, Tables 4, 5). Introduction of the D57S mutation reduced this calcium dependence. Consequently, the destabilising effect of the D57S mutant became smaller with decreasing calcium concentration; at the lowest calcium concentration tested, the wild-type enzyme was even slightly stabilised by the D57S mutation). The stability versus calcium concentration curves of TLP-ste and T63F-A69P (FIG. 5) can be superimposed remarkably well. The same is true for the D57S and the D57S-T63F-A69P, strongly suggesting that the observed effects on the calcium stability are indeed caused by the disturbance of the $Ca_3$ site by the D57S mutation.

The D57S-T63F-A69P mutant (referring to FIGS. 7A and 7B and SEQUENCE ID No. 2) represents a TLP-ste variant whose stability is largely independent of the calcium concentration and which, at lower calcium concentrations, is considerably more stable than the wild-type enzyme (Table 5). Combining known stabilising mutations in the $Ca_3$ region has resulted in extremely stable TLP-ste variants. Therefore, it is likely that mutants can be designed that are even less dependent on calcium than the ones described here and that are more stable. Also, and on the other hand, the knowledge now obtained about the calcium-binding site can be used to design variants that are still calcium-dependent while at the same time having obtained a much higher resistance to elevated temperatures or that are even resistant to boiling. Such enzymes can be used in reactions that require prolonged boiling but that can be stopped by changing the calcium concentration in the reaction mixture, by for example adding calcium or chelating agents that capture calcium, depending on the needs of the protease used. Engineering calcium-independence does not necessarily need to be based on detonating the $Ca_3$ site. Instead, it could be based on adding mutations that stabilise the local structure, regardless of the presence of a calcium ion. For example, preliminary analyses of a mutant in which the (intact) calcium binding site is covalently cross linked with the N-terminal β-hairpin showed that the stability of this mutant is also less calcium-dependent.

FURTHER EXAMPLE

Comparison of hydrolytic capacities of an 8-fold mutated TLP-ste variant (Boilysin) and commercial enzymes.

In industrial applications enzymes are used for the hydrolysis of protein preparations derived from different sources. Here we show the results of a comparative study in which the rate and quality of hydrolysis of casein and yeast protein preparations by the 8-fold mutated TLP-ste variant was compared with that obtained by the hydrolysis using 3 different enzyme preparations that are used for these purposes in industry. The hydrolysis conditions were chosen such that they were optimal for each of the enzyme preparation under study. The hydrolysis products were separated in an acid-soluble and a not acid-soluble fraction. The amount of acid-soluble protein material formed upon hydrolysis was determined by means of measuring the absorbance at 275 nm, whereas the composition of the acid-insoluble hydrolysis products was studied using SDS-PAGE.

Experimental

Substrate (10% w/v of casein or yeast protein preparation) was incubated in 50 mM Tris-MES, 5 mM $CaCl_2$, pH 6.5 at 50° C. (Enzyme I, Favourzyme™ 1000L); 50 mM Tris-MES, 5 mM $CaCl_2$, pH 6.0 at 60° C. (Enzyme II, BioProtease N100L); 50 mM Tris-MES, 5 mM $CaCl_2$, pH 8.0 at 60° C. (Enzyme III, Alcalase 2.4L); or in 50 mM Tris-MES, 5 mM $CaCl_2$, pH 7.0 at 90° C. (Boilysin). Concentration of the enzymes used was 0.05% (v/v). Samples were withdrawn at different time points and transferred to 0° C. The solubilized protein fraction was separated from the non-soluble fraction by centrifugation. Acid-precipitable proteins were separated from the acid-soluble fraction by TCA precipitation. The amount of acid-soluble protein released by hydrolysis was determined by measuring the absorbance of the samples at 275 nm. The acid precipitated proteins were redissolved in 6 M urea and subsequently analysed by SDS-PAGE (15% running gel).

Results

FIG. 8 shows the acid-soluble protein (panel A) released upon hydrolysis of casein with the different enzyme preparations in time.

FIG. 9 shows the acid-soluble protein (panel A) released upon hydrolysis of yeast proteins with the different enzyme preparations in time.

Conclusion FIGS. 8.A and 9.A suggest that hydrolysis of casein and yeast proteins is more rapidly and that more acid-soluble protein products are produced by the 8-fold mutated TLP-ste variant, as compared to the other enzyme preparations. FIGS. 8.B and 9.B show that a much broader range of hydrolysis products is generated by hydrolysis with the 8-fold mutated TLP-ste variant than with the other enzymes tested.

FIGURE DESCRIPTION

Figure 1:
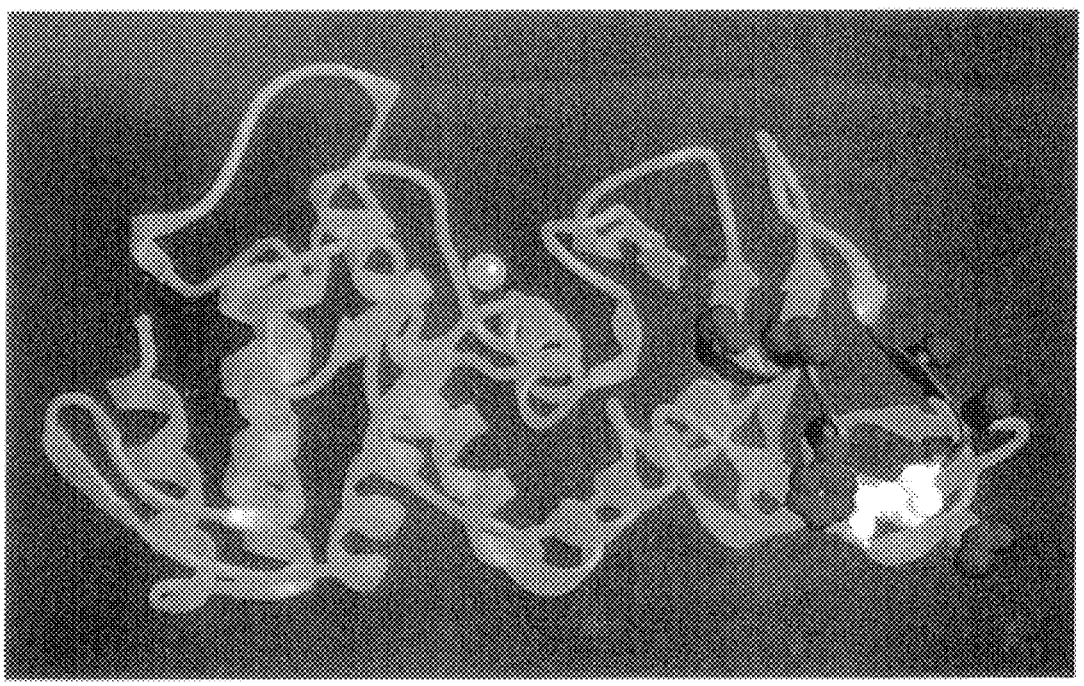
In FIG. 1, panel B the size-distribution of the not acid-soluble proteins obtained during hydrolysis of casein is depicted.

FIG. 1. Ribbon drawing of the three-dimensional model of the 8-fold mutated TLP-ste variant.

The model was constructed on the basis of homology with thermolysin (85% sequence identity) using WHAT IF. Compared to thermolysin (the amino acid sequence of which is shown in FIG. 7B or SEQUENCE ID No. 2), TLP-ste (the amino acid sequence of which is shown in FIG. 7A or SEQUENCE ID No. 1) contains three extra amino acids near position 27 which could not be modelled satisfactorily and were therefore omitted from the model. Considering the high sequence homology between thermolysin and TLP-ste, the model was expected to be sufficiently reliable to predict and analyse the effect of the amino acid substitutions. Details of the modelling procedures used to design and analyse mutations have been described elsewhere. Details of the design and construction of the disulfide bridge, as well as an extensive analysis of the effects of introducing this bridge in TLP-ste will be described elsewhere. Referring to FIGS. 7A and 7B and SEQUENCE ID No. 2, the 8–60 bridge was, in geometrical terms, the most promising disulfide bridge that was found in a search for possibly stabilizing disulfide bridges affecting the 55–69 region in TLP-ste. The 55–69 region is shown in blue. The side chains for the amino acids that were mutated in this study (A4T, T56A, G58A, T63F, S65P, A69P) are given in red and the disulfide bridge cross-linking residue 60 (N60C) in the critical region with residue 8 (G8C) in the underlying β-hairpin is shown in yellow. The light-blue sphere indicates the catalytic zinc ion.

Figure 2:
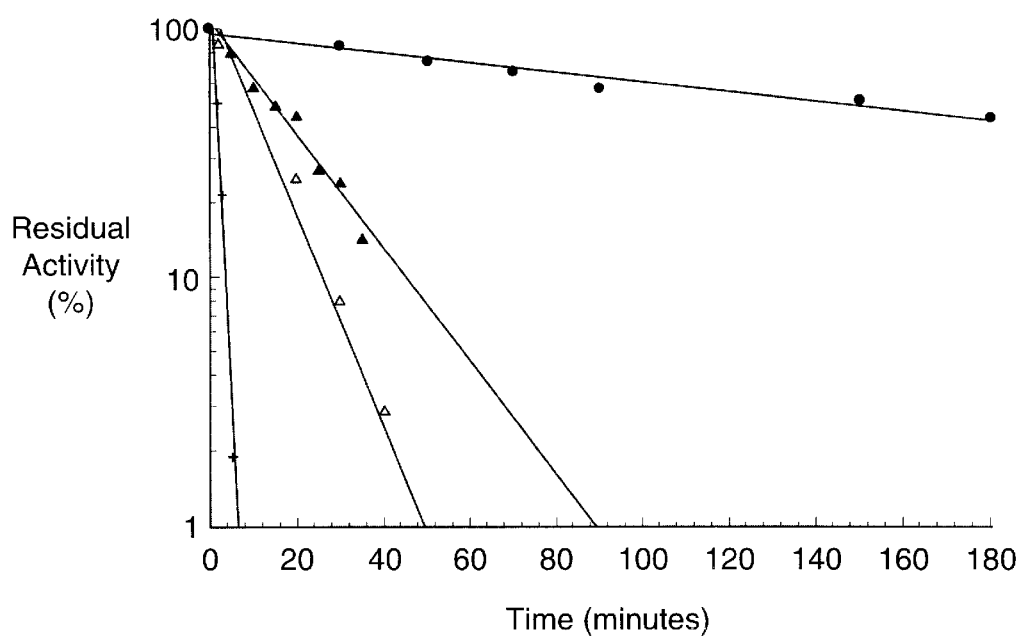
In FIG. 2, panel B the size-distribution of the not acid-soluble proteins obtained during hydrolysis of this protein mixture by the four enzymes is shown.

FIG. 2. Typical first-order inactivation of TLPs.

Stabilities of TLPs were determined at different temperatures. Shown are the first-order inactivation curves for TLP-ste incubated at 80° C. (Δ) and 90° C. (+), thermolysin at 90° C. (Δ), and the 8-fold mutant at 100° C. (●), respectively. For the determination of their half-lifes, the proteases were incubated in 20 mM NaAc (pH 5.3), 15 mM $CaCl_2$, 62.5 mM NaCl, 0.5% isopropanol, 0.01% Triton X-100, at 80, 90 or 100° C. Samples, taken at the various time points, were quickly cooled on ice (15 s) and transferred to 50° C. to prevent cold denaturation. Residual activity was determined using casein (0.8%) as a substrate in 50 mM TrisHCl (pH 7.5), 5 mM $CaCl_2$ as described previously (Eijsink, V. G. H., Veltman, O. R., Aukema, W., Vriend, G. & Venema, G. Nature Struct. Biol. 2, 374–379 (1995)).

Figure 3:
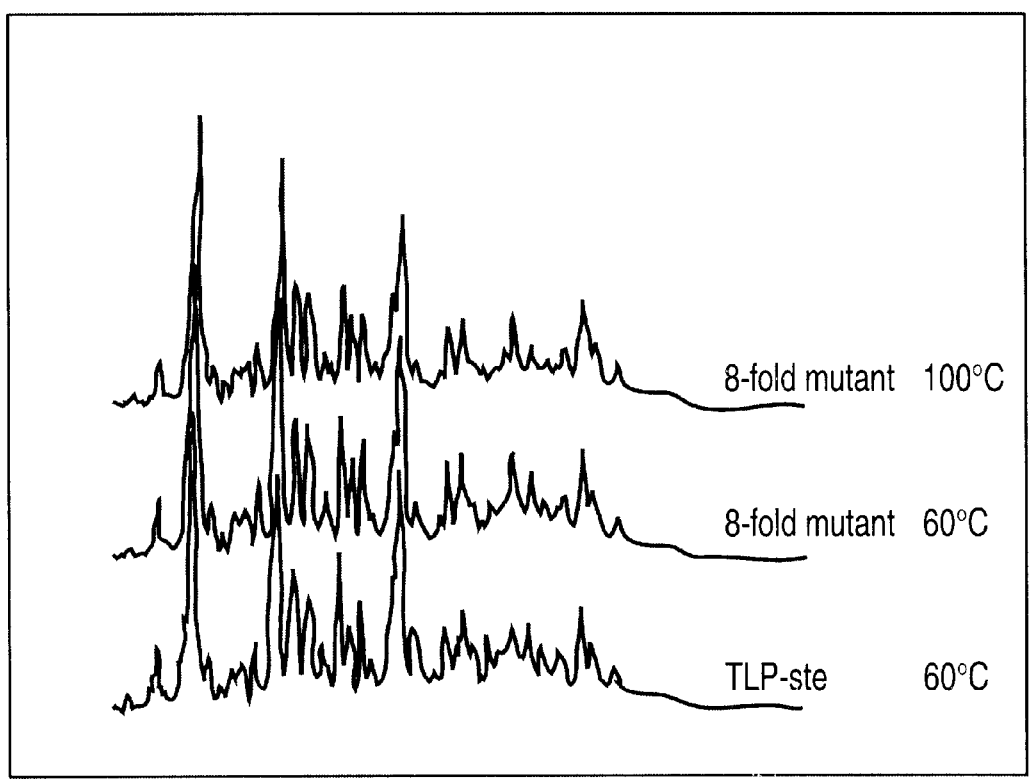

FIG. 3. Typical proteolytic specificity of TLP-ste and the 8-fold mutant β-Casein (1 mg/ml) was incubated with TLP-ste or the 8-fold mutant at a molar ratio of 1000:1 for 1 hour at 60° C. and 100° C., respectively. Under these conditions β-casein behaves as a non-compact and largely flexible structure. The peptides resulting from hydrolysis were derivatized with dansyl-chloride. The proteolytic products were separated by loading a sample corresponding to 50 μg β-casein on a reversed phase column (RP-304, Bio-Rad Laboratories, Watford, Herts., UK). The mobile phase used was 50 mM NaAc, pH 5.2. Peptides were eluted with a linear gradient from 0–60% acetonitrile at a flow rate of 1 ml/min. Absorption of the eluting peptides was monitored at 254 nm.

Figure 4:
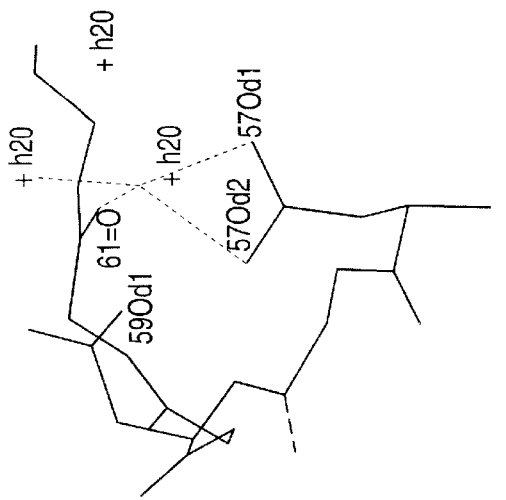
Figure 4:
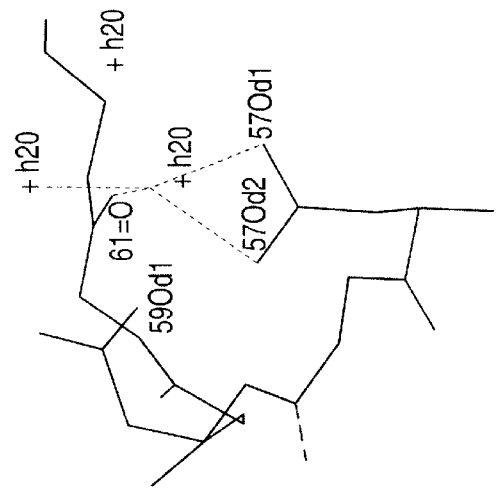
Figure 4:
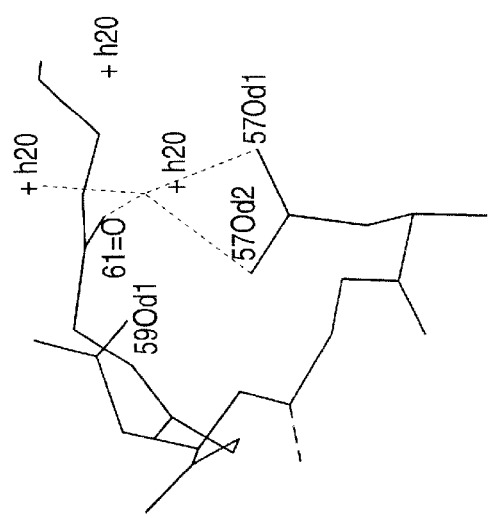

FIG. 4. Structure of the calcium binding site 3 ($Ca_3$) in thermolysin.

Crystal waters are indicated by crosses. Dashed lines indicate contacts of the $Ca_3$ atom with surrounding residues and crystal waters. Odi and Od2 indicate the side chain oxygen atoms of the Asp residues (Odi and Od2, respectively). In the region depicted in this figure, the model is virtually identical to the crystal structure of thermolysin.

Figure 5:
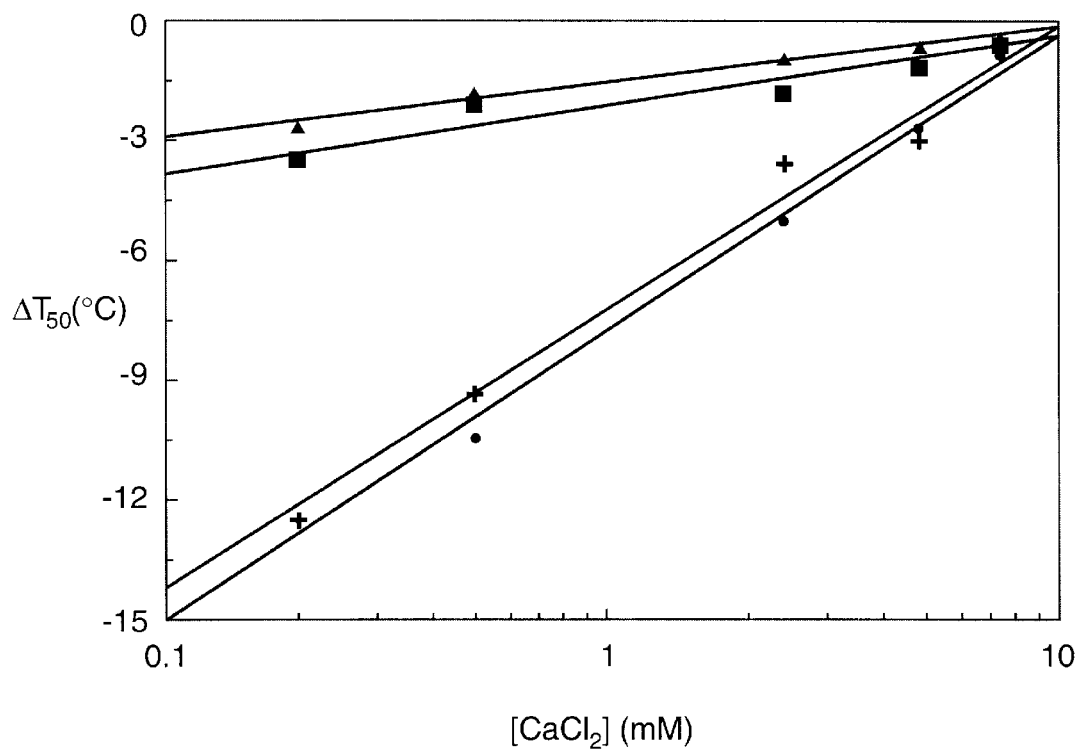

FIG. 5. Typical effects of the calcium concentration on $T_{50}$ for the wild-type (●), the D57S mutant (■), the T63F-A69P mutant (+) and the D57S-T63F-A69P mutant (Δ) (all of the amino acid sequence numbering being referred to in FIGS. 7 and 7B and in SEQUENCE ID No. 2).

$DT_{50}$ is the change in $T_{50}$ upon lowering the calcium concentration. The $T_{50}$ at 12.5 mM $CaCl_2$ is used as reference value ($DT_{50}=0$).

Figure 6A:
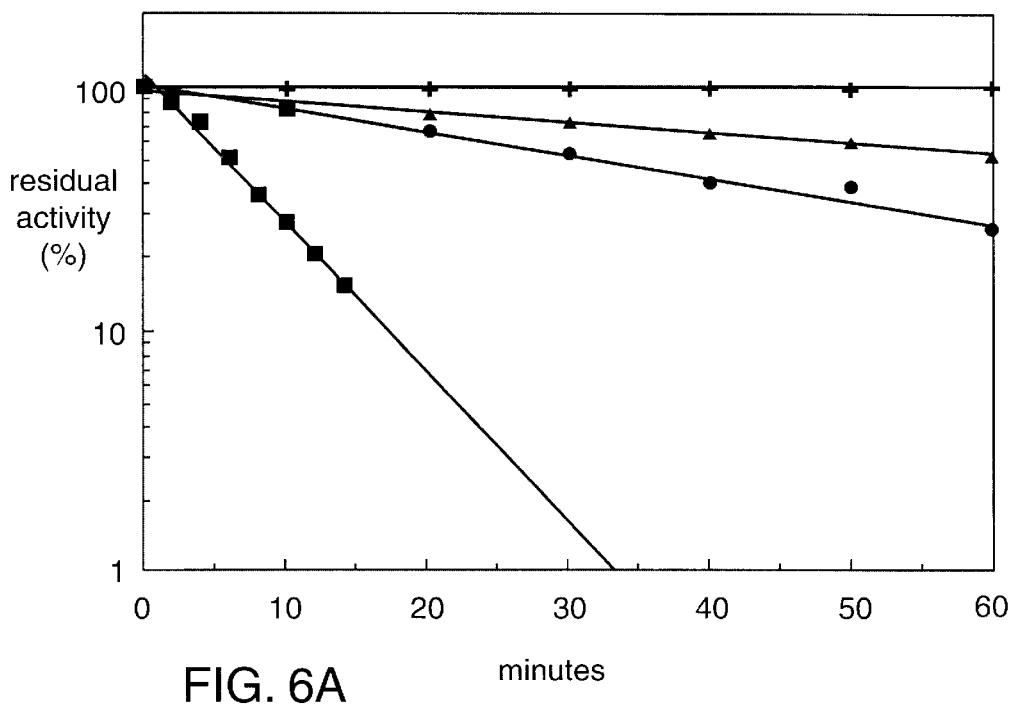
Figure 6B:
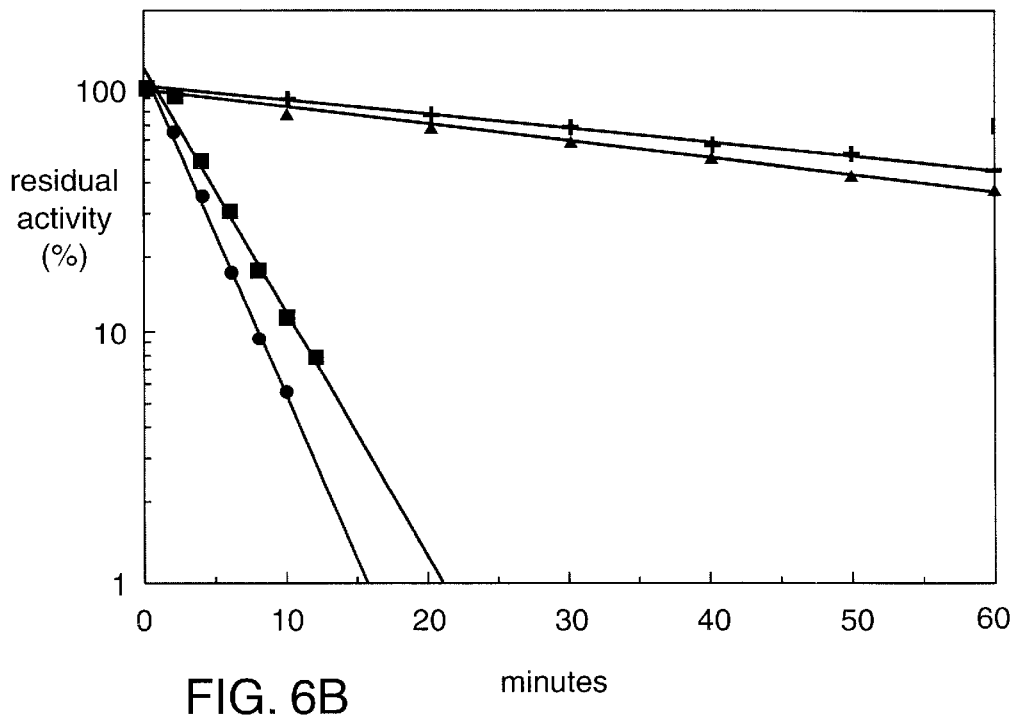

FIGS. 6(A & B). Typical first order thermal inactivation of TLP-ste variants at 75° C.; in (A) 5 mM $CaCl_2$ and (B) 0.2 mM $CaCl_2$; wildtype TLP-ste (●), D57S (■), T63F-A69P (+), D57S-T63F-A69P (Δ) (all of the amino acid sequence numbering being referred to in FIGS. 7 and 7B and in SEQUENCE ID No. 2).

FIG. 7A. Amino acid sequence (319 residues) of the mature extracellular TLP-ste protease or metalloendopeptidase secreted by *Bacillus stearothermophilus* (TLP-ste). FIG. 7A corresponds to SEQUENCE ID No. 1.

FIG. 7B. Amino acid sequence (316 residues) of the protease secreted by *Bacillus thermoproteolyticus* (thermolysin). FIG. 7B corresponds to SEQUENCE ID No. 2. Thus, in FIG. 7A, specifically, the only insertion/deletion in the alignment of thermolysin (316 residues) and TLP-ste (319 residues) is a three residue insertion between residues 25 and 30, shown parenthetically in FIG. 7A immediately after Ser27 as Ser Tyr Tyr. The TLP-ste contains the three residues, and the thermolysin does not contain the three residues. This insertion was omitted in the model for TLP-ste. In FIG. 7A, the TLP-ste residues are thus numbered according to the corresponding residues in thermolysin.

FIGS. 8(A, B & C). Hydrolysis of 10% (w/v) casein by different enzyme preparations (0.05%, v/v).

FIGS. 9(A, B & C). Hydrolysis of 10% (w/v) yeast proteins by different enzyme preparations (0.05%, v/v).

TABLE 3

Thermal stabilities ($T_{50}$) at varying concentrations of $CaCl_2$ of *B. stearothermophilus* thermolysin-like protease variants.

| [$CaCl_2$] (mM) | TLP ste $T_{50}$ (° C.) | D57S $T_{50}$ (° C.) | T63F-A69P $T_{50}$ (° C.) | D57S-T63F-A69P $T_{50}$ (° C.) |
|---|---|---|---|---|
| 0.2 | 65.5 | 65.9 | 77.8 | 74.6 |
| 0.5 | 67.5 | 67.3 | 80.9 | 75.4 |
| 2.5 | 72.9 | 67.5 | 86.6 | 76.2 |
| 5.0 | 75.2 | 68.2 | 87.2 | 76.5 |
| 7.5 | 77.0 | 68.8 | 89.7 | 76.7 |
| 12.5 | 77.9 | 69.4 | 90.2 | 77.2 |

Error margins in the $T_{50}$ values were in the range of 0.3–0.5° C.

TABLE 4

Activity and stability of TLP-ste variants.

| Variant | FaGLa, $k_{cat}/K_m$ × $10^{-3}$ ($M^{-1} \cdot S^{-1}$) | t½ at 5 mM $CaCl_2$ (min) | t½ at 0.2 mM $CaCl_2$ (min) | Half-life ratio 5 mM/0.2 mM |
|---|---|---|---|---|
| TLP-ste | 34 | 31 | 2.6 | 12 |
| D57S | 22 | 5.8 | 3.8 | 1.5 |
| T63F-A69P | 21 | 990 | 52 | 19 |
| D57S-T63F-A69P | 28 | 64 | 42 | 1.5 |

The activity against FaGLa was determined at 37° C. Half-lives (t½) were calculated from the inactivation curves shown in FIGS. 3a and b. The t½ value of the T63F-A69P mutation (referring to FIGS. 7 and 7B and SEQUENCE ID No. 2) was extrapolated from the data presented in FIG. 3a. The error margins in the t½ values are less than 4%.

TABLE 1

| | enzymatic properties at 37° C. | | | | | stability | | | |
|---|---|---|---|---|---|---|---|---|---|
| | Specific activity | $k_{cat}/K_m$ | | | | | half-lifes | | |
| | casein | FaGLa | | $K_i$ | | | | | |
| | (U/mg) × $10^{-3}$ | ($M^{-1}.s^{-1}$) × $10^{-3}$ | FaAFa ($M^{-1}.s^{-1}$) | phosphoramidon (mM) | $T_{opt}$ (° C.) | 80° C. (min.) | 90° C. (min.) | 100° C. (min.) |
| TLP-ste | 3.5 ± 0.7 | 30 ± 8 | 222 ± 33 | 50 ± 18 | 74 | 17.5 | <2 | <0.5 |
| TLN | n.a. | n.a. | n.a. | n.a. | 77 | >200 | 12.5 | <2 |
| 8-fold mutant | 3.9 ± 0.7 | 30 ± 6 | 266 ± 23 | 43 ± 13 | 95 | stable | stable | 170 |

TABLE 2

Effect of denaturing agents on protease activity

| GndHCl | relative activity | | Urea | relative activity | | SDS | relative activity | |
|---|---|---|---|---|---|---|---|---|
| (M) | TLP-ste | 8-fold mutant | (M) | TLP-ste | 8-fold mutant | (% w/v) | TLP-ste | 8-fold |
| 0 | 100 | 100 | 0 | 100 | 100 | 0 | 100 | 100 |
| 1.0 | 99 | 95 | 0.5 | 96 | 97 | 0.25 | 72 | 94 |
| 2.0 | 62 | 83 | 1.0 | 87 | 91 | 0.5 | 37 | 81 |
| 3.0 | 0 | 68 | 2.0 | 75 | 93 | 0.75 | 9.6 | 57 |
| 4.0 | 0 | 50 | 3.0 | 3 | 86 | 1.0 | 0 | 40 |
| 5.0 | 0 | 40 | 4.0 | 0 | 72 | 1.25 | 0 | 29 |
| 5.5 | 0 | 15 | 5.0 | 0 | 63 | 1.5 | 0 | 22 |
| 6.0 | 0 | 0 | 7.5 | 0 | 35 | 2.0 | 0 | 0 |

What is claimed is:

1. A recombinant DNA molecule coding for a polypeptide with SEQ ID No.1 or SEQ ID No.2 having a thermolysin-like protease and metallo-endopeptidase activity wherein (i) in SEQUENCE ID No. 2 the codon coding for N at position 60 and the codon coding for G at position 8 have been mutated to code for cysteine to generate a stabilizing disulfide bridge and (ii) in SEQUENCE ID No. 1 the codon coding for N at position 63 and the codon coding for G at position 8 have been mutated to code for cysteine to generate a stabilizing disulfide bridge.

2. A recombinant DNA molecule comprising a DNA molecule according to claim 1 wherein the codon coding for D at position 57 of SEQUENCE ID No. 2 or position 60 of SEQUENCE ID No. 1 is mutated to code for an amino acid providing the gene product with (i) a reduced capacity to bind with calcium and (ii) a stability, that is less dependent on calcium and more stable than found with a wild-type thermolysin-like protease with a half-life at 0.2 mM CaCl$_2$ of 2.6 minutes.

3. A recombinant DNA molecule comprising a DNA molecule according to claim 1 wherein (i) in SEQUENCE ID No. 2, one codon coding for A at position 4, or T at position 56, or G at position 58, or T at position 63, or S at position 65, or A at position 69 is also mutated, or (ii) in SEQUENCE ID No. 1, one codon coding for A at position 4, or T at position 59, or G at position 61, or T at position 66, or S at position 68, or A at position 72, is also mutated.

4. A recombinant DNA molecule according to claim 3 wherein (i) in SEQUENCE ID No. 2 one codon encoding the amino acid at position 4 is replaced by a codon encoding T, or at position 56 by a codon encoding A, or at position 58 by a codon encoding A, or at position 63 by a codon encoding F, or at position 65 by a codon encoding P, or at position 69 by a codon encoding P, or (ii) in SEQUENCE ID No. 1 one codon encoding the amino acid at position 4 is replaced by a codon encoding T, or at position 59 by a codon encoding A, or at position 61 by a codon encoding A, or at position 66 by a codon encoding F, or at position 68 by a codon encoding P, or at position 72 by a codon encoding P.

5. A recombinant DNA molecule comprising a DNA molecule according to claim 1 wherein (i) in SEQUENCE ID No. 2, the codon coding for D at position 57 has been mutated to code for serine, or (ii) in SEQUENCE ID No. 1, the codon coding for D at position 60 has been mutated to code for serine.

6. A vector for expression of a polypeptide having thermolysin-like protease and metallo-endopeptidase activity in a host cell comprising a recombinant DNA molecule according to claim 1.

7. A host cell for expression of a polypeptide having thermolysin-like protease and metallo-endopeptidase activity comprising a vector according to claim 6.

8. A method for producing a polypeptide having thermolysin-like protease and metallo-endopeptidase activity comprising the steps of:
  (a) culturing the host cell defined according to claim 7;
  (b) effecting the expression of said polypeptide having thermolysin-like protease and metallo-endopeptidase activity from said host cell; and
  (c) purifying the resulting expressed polypeptide.

9. A recombinant polypeptide having thermolysin-like protease and metallo-endopeptidase activity produced according to the process of claim 6.

10. The recombinant DNA molecule of claim 1 coding for a mutated metallo-endopeptidase from *B. stearothermophilus*.

11. The vector of claim 6 which is a vector for expression of a mutated metallo-endopeptidase from *B. stearothermophilus*.

12. The method of claim 8 which is a method for producing a mutated metallo-endopeptidase from *B. stearothermophilus*.

13. The mutated metallo-endopeptidase from *B. stearothermophilus* having metallo-endopeptidase activity produced according to the process of claim 12.

* * * * *

SEQUENCE LISTING

<160> NUMBER OF SEQ ID NOS: 2

<210> SEQ ID NO 1
<211> LENGTH: 319
<212> TYPE: PRT
<213> ORGANISM: Bacillus sp.

<400> SEQUENCE: 1

```
Val Ala Gly Ala Ser Thr Val Gly Val Gly Arg Gly Val Leu Gly Asp
 1               5                  10                  15

Gln Lys Tyr Ile Asn Thr Thr Tyr Ser Ser Tyr Tyr Gly Tyr Tyr Tyr
                20                  25                  30

Leu Gln Asp Asn Thr Arg Gly Ser Gly Ile Phe Thr Tyr Asp Gly Arg
            35                  40                  45

Asn Arg Thr Val Leu Pro Gly Ser Leu Trp Thr Asp Gly Asp Asn Gln
        50                  55                  60

Phe Thr Ala Ser Tyr Asp Ala Ala Val Asp Ala His Tyr Ala
65                  70                  75                  80

Gly Val Val Tyr Asp Tyr Tyr Lys Asn Val His Gly Arg Leu Ser Tyr
                85                  90                  95

Asp Gly Ser Asn Ala Ala Ile Arg Ser Thr Val His Tyr Gly Arg Gly
            100                 105                 110

Tyr Asn Asn Ala Phe Trp Asn Gly Ser Gln Met Val Tyr Gly Asp Gly
        115                 120                 125

Asp Gly Gln Thr Phe Leu Pro Phe Ser Gly Gly Ile Asp Val Val Gly
    130                 135                 140

His Glu Leu Thr His Ala Val Thr Asp Tyr Thr Ala Gly Leu Val Tyr
145                 150                 155                 160

Gln Asn Glu Ser Gly Ala Ile Asn Glu Ala Met Ser Asp Ile Phe Gly
                165                 170                 175

Thr Leu Val Glu Phe Tyr Ala Asn Arg Asn Pro Asp Trp Glu Ile Gly
            180                 185                 190

Glu Asp Ile Tyr Thr Pro Gly Val Ala Gly Asp Ala Leu Arg Ser Met
        195                 200                 205

Ser Asp Pro Ala Lys Tyr Gly Asp Pro His Tyr Ser Lys Arg Tyr
    210                 215                 220

Thr Gly Thr Gln Asp Asn Gly Gly Val His Thr Asn Ser Gly Ile Ile
225                 230                 235                 240

Asn Lys Ala Ala Tyr Leu Leu Ser Gln Gly Gly Val His Tyr Gly Val
                245                 250                 255

Ser Val Asn Gly Ile Gly Arg Asp Lys Met Gly Lys Ile Phe Tyr Arg
            260                 265                 270

Ala Leu Val Tyr Tyr Leu Thr Pro Thr Ser Asn Phe Ser Gln Leu Arg
        275                 280                 285

Ala Ala Cys Val Gln Ala Ala Asp Leu Tyr Gly Ser Thr Ser Gln
    290                 295                 300

Glu Val Asn Ser Val Lys Gln Ala Phe Asn Ala Val Gly Val Tyr
305                 310                 315
```

<210> SEQ ID NO 2
<211> LENGTH: 316
<212> TYPE: PRT
<213> ORGANISM: Bacillus sp.

<400> SEQUENCE: 2

-continued

```
Val Ala Gly Ala Ser Thr Val Gly Val Gly Arg Gly Val Leu Gly Asp
1               5                   10                  15

Gln Lys Tyr Ile Asn Thr Thr Tyr Ser Gly Tyr Tyr Tyr Leu Gln Asp
                20                  25                  30

Asn Thr Arg Gly Ser Gly Ile Phe Thr Tyr Asp Gly Arg Asn Arg Thr
            35                  40                  45

Val Leu Pro Gly Ser Leu Trp Thr Asp Gly Asp Asn Gln Phe Thr Ala
        50                  55                  60

Ser Tyr Asp Ala Ala Ala Val Asp Ala His Tyr Tyr Ala Gly Val Val
65                  70                      75                  80

Tyr Asp Tyr Tyr Lys Asn Val His Gly Arg Leu Ser Tyr Asp Gly Ser
                85                  90                  95

Asn Ala Ala Ile Arg Ser Thr Val His Tyr Gly Arg Gly Tyr Asn Asn
                100                 105                 110

Ala Phe Trp Asn Gly Ser Gln Met Val Tyr Gly Asp Gly Asp Gly Gln
            115                 120                 125

Thr Phe Leu Pro Phe Ser Gly Gly Ile Asp Val Val Gly His Glu Leu
        130                 135                 140

Thr His Ala Val Thr Asp Tyr Thr Ala Gly Leu Val Tyr Gln Asn Glu
145                 150                 155                 160

Ser Gly Ala Ile Asn Glu Ala Met Ser Asp Ile Phe Gly Thr Leu Val
                165                 170                 175

Glu Phe Tyr Ala Asn Arg Asn Pro Asp Trp Glu Ile Gly Glu Asp Ile
            180                 185                 190

Tyr Thr Pro Gly Val Ala Gly Asp Ala Leu Arg Ser Met Ser Asp Pro
        195                 200                 205

Ala Lys Tyr Gly Asp Pro Asp His Tyr Ser Lys Arg Tyr Thr Gly Thr
    210                 215                 220

Gln Asp Asn Gly Gly Val His Thr Asn Ser Gly Ile Ile Asn Lys Ala
225                 230                 235                 240

Ala Tyr Leu Leu Ser Gln Gly Gly Val His Tyr Gly Val Ser Val Asn
                245                 250                 255

Gly Ile Gly Arg Asp Lys Met Gly Lys Ile Phe Tyr Arg Ala Leu Val
            260                 265                 270

Tyr Tyr Leu Thr Pro Thr Ser Asn Phe Ser Gln Leu Arg Ala Ala Cys
    275                 280                 285

Val Gln Ala Ala Ala Asp Leu Tyr Gly Ser Thr Ser Gln Glu Val Asn
    290                 295                 300

Ser Val Lys Gln Ala Phe Asn Ala Val Gly Val Tyr
305                 310                 315
```